US012207977B2

(12) United States Patent  
Allen

(10) Patent No.: US 12,207,977 B2
(45) Date of Patent: Jan. 28, 2025

(54) SUPPORT ASSEMBLY FOR OPHTHALMIC VISUALIZATION SYSTEM

(71) Applicant: Alcon Inc., Fribourg (CH)

(72) Inventor: Douglas Allen, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 16 days.

(21) Appl. No.: 18/362,512

(22) Filed: Jul. 31, 2023

(65) Prior Publication Data

US 2024/0041556 A1 Feb. 8, 2024

Related U.S. Application Data

(60) Provisional application No. 63/396,068, filed on Aug. 8, 2022.

(51) Int. Cl.
*A61B 90/25* (2016.01)
*A61F 9/007* (2006.01)
*A61B 90/00* (2016.01)

(52) U.S. Cl.
CPC .............. *A61B 90/25* (2016.02); *A61F 9/007* (2013.01); *A61B 2090/373* (2016.02)

(58) Field of Classification Search
CPC .............. A61B 90/25; A61B 2090/373; A61B 2090/502; A61B 2090/508; A61B 2090/571; A61B 90/50; A61B 3/0041; A61F 9/007
USPC .......................................................... 348/78
See application file for complete search history.

(56) References Cited

U.S. PATENT DOCUMENTS

| | | | |
|---|---|---|---|
| 2006/0135866 A1 | 6/2006 | Namii | |
| 2014/0005485 A1* | 1/2014 | Tesar | A61B 17/1628 600/201 |
| 2015/0085095 A1* | 3/2015 | Tesar | A61B 34/20 359/613 |
| 2015/0230866 A1 | 8/2015 | Tung | |
| 2017/0042419 A1 | 2/2017 | Nakanishi | |
| 2017/0273715 A1* | 9/2017 | Piron | A61B 34/30 |
| 2018/0177523 A1* | 6/2018 | Piron | A61B 5/0062 |
| 2019/0125182 A1* | 5/2019 | Charles | A61B 3/0033 |
| 2021/0335483 A1* | 10/2021 | Freeman | G16H 50/20 |
| 2022/0087711 A1* | 3/2022 | Piron | A61B 34/30 |

(Continued)

FOREIGN PATENT DOCUMENTS

| | | |
|---|---|---|
| DE | 3703424 A1 | 10/1987 |
| JP | 6989228 B2 | 12/2021 |
| WO | 2016108276 A1 | 7/2016 |

*Primary Examiner* — Marnie A Matt

(57) ABSTRACT

The present disclosure relates to visualization systems system for surgical procedures, and more specifically, to an imaging and display support system for ophthalmic visualization systems. The optical system described herein provide improved ergonomics for surgeons, as such systems incorporate an optical head and a corresponding display on a single support arm to provide surgeons a direct and unobstructed view of the corresponding display screen placed in an ergonomically advantageous position for ophthalmic procedures. Such systems also maintain the corresponding display screen in the aforementioned in an ergonomically advantageous position even if the optical head of the system is moved or rotated during ophthalmic procedures without the need for further adjustments by the surgeon or surgical staff.

20 Claims, 9 Drawing Sheets

(56) References Cited

U.S. PATENT DOCUMENTS

| | | | |
|---|---|---|---|
| 2023/0120611 A1* | 4/2023 | Polchin | A61B 90/50 348/47 |
| 2023/0141727 A1* | 5/2023 | Myers | A61B 3/132 351/206 |

* cited by examiner

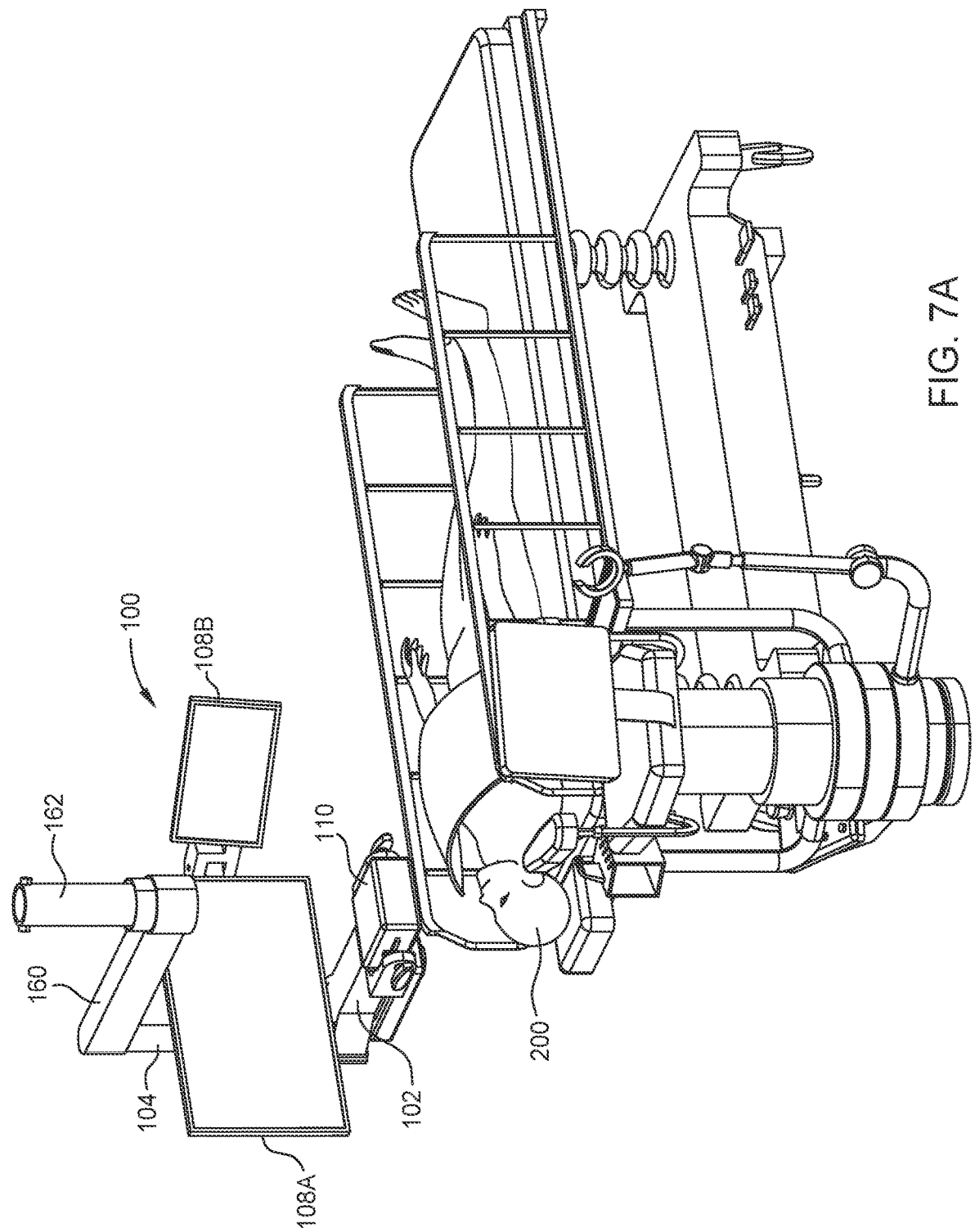

SUPPORT ASSEMBLY FOR OPHTHALMIC VISUALIZATION SYSTEM

BACKGROUND

Vitreoretinal and cataract surgical procedures are among the most commonly performed ophthalmic surgical procedures. As the name implies, vitreoretinal procedures are performed in the gel-like vitreous and on surfaces of the light-sensitive retina within the relatively small ocular space. Common conditions necessitating vitreoretinal surgery include epimacular membranes, vitreomacular schisis, vitreomacular traction syndrome, diabetic traction retinal detachments, proliferative vitreoretinopathy (PVR), retinal detachment, macular holes, as well as other various conditions necessitating micro-injection procedures for gene and cell based therapies. Cataract surgeries, on the other hand, involve the removal of a cloudy natural lens of the eye, and replacing it with a new artificial lens. There are generally two types of cataract surgeries: phacoemulsification, wherein the cloudy lens is removed after being broken up by application of ultrasound waves, and extracapsular surgery, wherein the cloudy core of the lens is removed in one piece.

Traditionally, surgeons performing vitreoretinal and/or cataract surgeries utilized surgical microscope eyepieces to provide magnified and illuminated images of ophthalmic structures within the eye. More recently, however, advances in imaging technology have led to the use of heads-up digital surgical visualization systems. Such visualization systems, which rely on high-resolution stereoscopic cameras and/or microscopes to transmit images from the patient's eye to a heads-up display screen for viewing by the surgeon, offer the advantages of better ergonomics for the surgeon, reduced phototoxicity, peripheral visualization, and improved magnification as compared to traditional microscopes.

Although there are many benefits associated with the use of heads-up digital surgical visualization systems, such systems still have many constraints. One major drawback of some systems is the impedance of the line of sight between the surgeon and a corresponding heads-up display showing the microscopic images captured by the system's camera(s). For example, in purely digital systems where only a camera and display are used, problems may arise due to the camera needing to be 150-200 mm (working distance) above the patient's eye. The combination of the necessary working distance and the camera's associated height can create an obstruction, thereby impeding the ideal line of sight between the surgeon and the display. Similarly, in systems utilizing digital microscopes or microscopes integrated with digital cameras, the corresponding display is often placed beside the microscope, thereby requiring the surgeon to employ a less-than-ideal ergonomic position to view the display while performing the surgical procedure.

Additionally, the microscope/camera(s) and heads-up displays for many digital surgical visualization systems are typically supported by separate support devices, which can create unnecessary hardship when adjusting such components in between surgical procedures. For example, for ophthalmic surgical procedures, there are three primary positions that the surgeon may assume in relation to the patient's head: left temporal, right temporal, and superior. For each position, display(s) and associated equipment must be moved to certain positions to ensure the surgeon has a clear line of sight to the center of the display(s). Ergonomically, the system should also be arranged such that the surgeon's head is level and not turned when viewing the display(s). Further, to provide the surgeon with an immersive 3D effect, the surgeon's display will also need to be positioned at a specific distance from the surgeon. As such, the display(s) and associated equipment for a digital surgical visualization system, as well as other equipment in the operating room, must be set up before a surgical procedure based on the position the surgeon will be assuming during the surgical procedure.

If a position to be assumed by the surgeon in a subsequent procedure in the operating room is different from the last procedure performed therein, the display(s) and other associated equipment of the digital surgical visualization system may need to be moved and/or adjusted to correspond with the new position. Thus, maintaining good ergonomics for the surgeon during sequential surgical procedures can be particularly challenging if different components of a digital surgical visualization system are supported by separate devices, which can each require individual adjustments to support different positions of the surgeon during surgical procedures. Such repositioning of the equipment may be so taxing and time-consuming for surgical staff that surgical procedures end up being scheduled based upon the position to be employed by the surgeon in order to reduce the amount of repositioning of the equipment throughout the day. However, such scheduling accommodations may not always be feasible in surgical emergency situations.

Thus, the combination of camera and/or microscope geometry, as well as the mounting of camera(s) and corresponding monitors on separate support structures, can create a setting of poor ergonomics for surgeons during ophthalmic surgical procedures that can affect both the procedure and the outcome. Accordingly, there is a need in the art for improved support devices for surgical visualization systems.

SUMMARY

Embodiments of the present disclosure relates to visualization systems for surgical procedures, and more specifically, to an imaging and display support system for ophthalmic visualization systems.

In certain embodiments, a support system for an ophthalmic visualization system is provided, the support system comprising: a base column; a first arm connected to the base column, wherein the first arm is configured to rotationally translate along a first horizontal plane and about a first revolute joint at the base column; an optical head coupled to the first arm; and a first display coupled to a top surface of the first arm.

In another embodiment, a support system for an ophthalmic visualization system is provided, the support system comprising a base column; a base arm comprising a proximal end and a distal end wherein the proximal end of the base arm coupled to the base column via the first revolute joint, and the distal end of the base arm is connected to a support column extending between the base arm and a proximal end of a first arm; an optical head coupled to a distal end of the first arm; a first display coupled to a top surface of the first arm; and wherein translation of the base arm along a second horizontal plane parallel to the first horizontal plane about the first revolute joint simultaneously causes translation of the first arm along a first horizontal plane.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIGS. 7A-7C illustrate perspective views of the visualization system arm assembly of FIG. 1 positioned in a right temporal, a left temporal, and a superior position about a patient, respectively, in accordance with certain embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
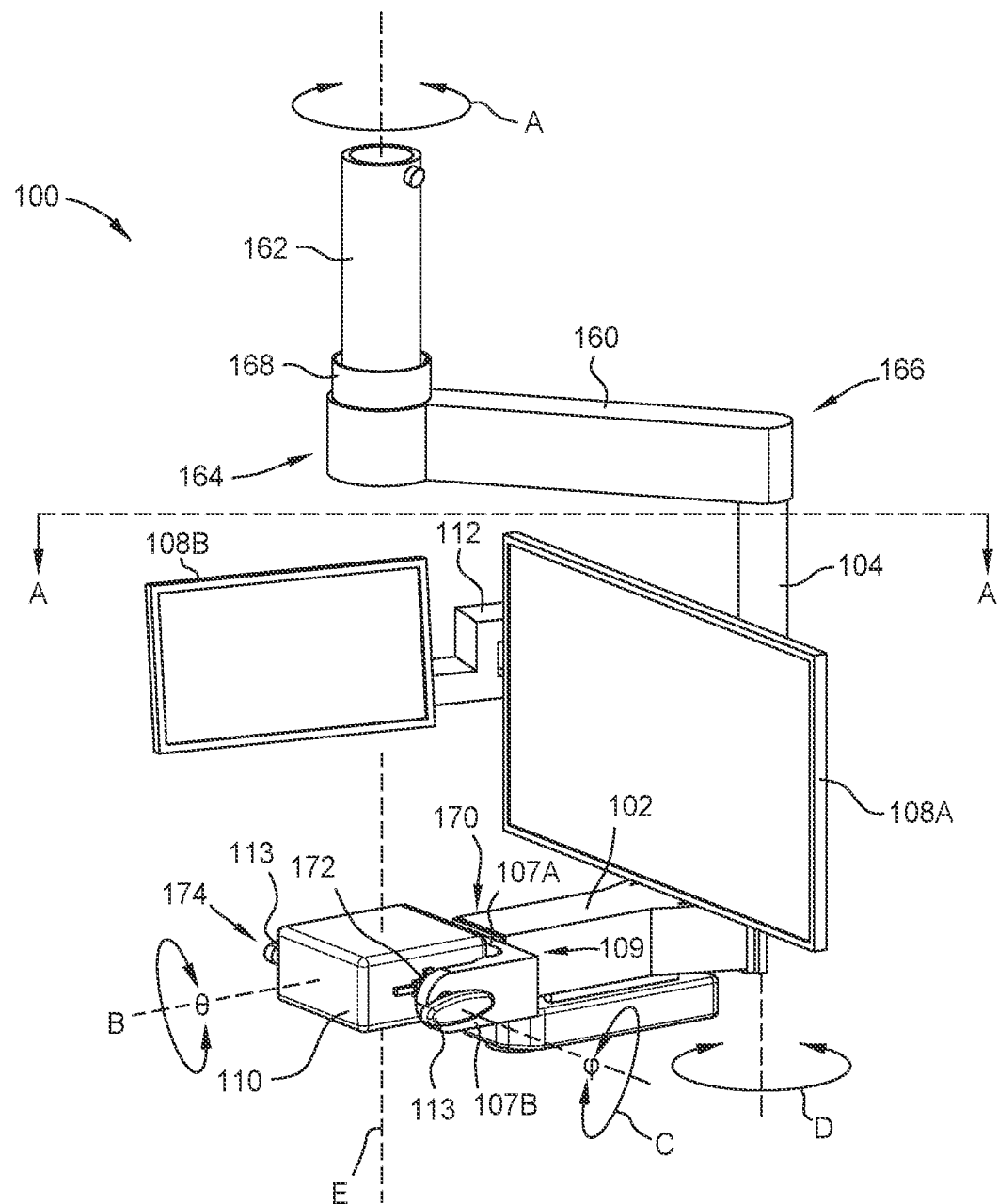
FIG. 1 illustrates a perspective view of an exemplary visualization system arm assembly in use during an ophthalmic surgical procedure, in accordance with certain embodiments of the present disclosure.

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's target tissue during use thereof. On the other hand, a proximal end, segment, or portion of the component refers to the end, segment, or portion that is distanced further away from the patient's target tissue.

As used herein, the term "about" may refer to a +/−10% variation from the nominal value. It is to be understood that such a variation can be included in any value provided herein.

The present disclosure relates to visualization systems for surgical procedures, and more particularly, to support systems for heads-up digital visualization systems that can be used during ophthalmic surgical procedures. As discussed above, conventional heads-up digital surgical visualization systems may not be optimized for ophthalmic surgeries in terms of ergonomics. For example, such digital surgical visualization systems may have displays mounted to the side of the microscope and/or camera, thereby requiring the surgeon to employ a less-than-ideal ergonomic position to view the display while performing a surgical procedure. Further, in systems where the imaging device and the corresponding display are mounted to separate support assemblies, having to separately readjust and change positions of the imaging device and/or display every time the surgeon assumes a different position for a subsequent procedure can be challenging for operating staff, and may unnecessarily delay procedures and increase transition times. The support assemblies described herein address the deficiencies of certain existing designs by providing a single mechanical arm assembly that supports both an optical head and associated heads-up display(s) for use with digital surgical visualization systems. Such support assemblies described herein further provide the surgeon and/or associated surgical team with unobstructed visual access to the heads-up displays showing the surgical target site, and therefore facilitate improved ergonomics for the surgeon and/or the surgical team during ophthalmic surgical procedures. The support assembly described herein may also be repositioned by the surgeon as needed during procedures with the aforementioned improved ergonomics being maintained during repositioning.

FIG. 1 illustrates an exemplary arm assembly for use with heads-up digital surgical visualization systems during ophthalmic surgical procedures, according to certain embodiments described herein. In the example of FIG. 1, visualization system arm assembly ("arm assembly") 100 is coupled to and supported by a horizontal base arm 160 extending from a vertical base column 162. The vertical base column 162 may extend downward and perpendicular to an operating room floor from a base structure (not shown), such as a boom arm assembly, a ceiling of the operating room, a robotic arm on a cart, and the like. The vertical base column 162 may be movably connected to the base structure such that the vertical base column 162 may be moved relative to the operating room to provide for gross movement and positioning of the arm assembly 100. The horizontal base arm 160 comprises a first end 164, a second end 166, and is rotatably coupled to the vertical base column 162 at the first end 164 via a base revolute joint 168 and to the arm assembly 100 at the second end 166. The horizontal base arm 160 may be configured to rotate about a vertical axis A extending through the base resolute joint 168 and vertical base column 162, thereby providing horizontal movement for the horizontal base arm 160 along a horizontal X-Y plane parallel to the floor relative to vertical base column 162. In certain embodiments, the base revolute joint 168 is configured to slide up and down along the vertical base column 162 to allow the horizontal base arm 160 to translate vertically along the vertical axis A while maintaining the horizontal and/or diagonal orientation of the horizontal base arm 160.

The arm assembly 100 comprises a horizontal support arm 102 extending from a vertical column 104 that is connected to the second end 166 of the horizontal base arm 160. The arm assembly 100 also includes an optical head 110, which is movably coupled to a distal end 109 of the horizontal support arm 102 opposite from the vertical column 104. The vertical column 104 extends downward and perpendicular to the operating room floor from the horizontal support arm 102. The vertical column 104 supports the horizontal support arm 102, thereby allowing the horizontal support arm 102 and the optical head 110 to be moved by the surgeon relative to a patient so as to align and properly orient the optical head 110 over the patient for the surgery.

In FIG. 1, the optical head 110 includes a single, low profile optical head to facilitate providing the surgeon standing opposite of the distal end 109 of the horizontal support 102 with a direct and unobstructed view of a primary heads-up display 108A. Generally, the optical head 110 may comprise one or more of the following optical devices: a microscope, a digital microscope, a compound microscope, a digital compound microscope, a digitally assisted microscope, a digital microscope camera, a digital camera, an ophthalmic 3D stereo microscope camera, and the like. Such devices may include any suitable optical and/or digital mechanisms for high-resolution imaging of ophthalmic structures in the eye of a patient being operated on.

In certain embodiments, the optical head 110 is rotatably connected to the distal end 109 of the horizontal support arm 102 by a yoke 107. The yoke 107 may operably enable fine and precise "roll" and "pitch" movements of the optical head 110, indicated by arrows φ and θ, respectively, to provide the surgeon dynamic views of the patient's eye when the optical head 110 is in use. Such "roll" and "pitch" movements are orthogonal to an optical axis "E" of the optical head 110. The yoke 107 includes a yoke base 107A and a pair of yoke arms 107B, 107C extending from opposite ends of the yoke base 107A. The pair of yoke arms 107B, 107C may extend parallel to one another from the yoke base 107A in the same direction such that the yoke 107 is formed in substantially the shape of a "U," wherein the optical head 110 is positioned between the yoke arms 107B, 107C within the "U." The yoke 107 is rotatably connected to the horizontal support arm 102 at the yoke base 107A by a revolute joint 170 such that the yoke 107 is configured to rotate about a longitudinal axis B of the horizontal support 102 to enable "roll" motion of the yoke 107 and thereby, the optical head 110, when the optical head 110 is connected to the yoke 107. As shown, the optical head 110 may be connected to each of the yoke arms 107B, 107C by a revolute joint 172, 174 such that the optical head 110 is configured to rotate about a lateral axis C perpendicular to the longitudinal axis B. The rotation of the optical head 110 about lateral axis C between the yoke arms 107B, 107C provide the optical head 110 with fine "pitch" movements.

In certain embodiment, the optical head 110 may also comprise one or more handles 113 for manually moving the optical head 110 and/or the connected horizontal support arm 102 about the vertical column 104. The one or more handles 113 may also be used to manually adjust the aforementioned "pitch" and "roll" motions of the optical head 110. In other embodiments, the assembly 100 may comprise one or more actuators, motors, and/or controllers such that control and movement of the "pitch" and "roll" motions of the optical head 110, as well as any horizontal translation of the horizontal support arm 102 and/or horizontal base arm 160, may be motorized. In such examples, movement of the assembly 100 may be controlled by the surgeon via a console, such as a surgical console (not shown).

As further shown in FIG. 1, the arm assembly 100 also includes one or more primary and/or secondary heads-up displays 108A, 108B (collectively, heads-up displays 108) for viewing images of the target surgical site as relayed by the optical head 110 and/or other image sources. For example, during an ophthalmic surgical procedure such as a vitreoretinal or cataract surgical procedure, camera(s) within the optical head 110 may relay magnified and illuminated images of ophthalmic structures in the eye of the patient to the heads-up display(s) 108 for viewing by the surgeon and any operating staff therewith. Accordingly, the surgeon (and operating staff) may view such images without having to look through the eyepieces of a microscope, thereby affording the advantage of better visual optics and ergonomics for the surgeon (and operating staff).

In the example shown in FIG. 1, the primary heads-up display 108A is affixed adjacent to a top surface of horizontal support arm 102. When the arm assembly 100 is in use, a surgeon may stand opposite of the distal end 109 of the horizontal support arm 102 such that the optical head 110 is positioned between the surgeon and the primary heads-up display 108A. In this position, the horizontal support arm 102 extends along a direction that the surgeon is facing, with the viewing portion of the primary heads-up display 108 disposed directly in front of (e.g., anterior to) the surgeon. Accordingly, when using arm assembly 100 in combination with a 3D visualization system during a surgical procedure, the angle of the surgeon's line of sight in relation to the primary heads-up display 108A may be disposed within the requisite limits of the 3D visualization system to create an optimal 3D effect. Additionally, to provide the most favorable ergonomics for the surgeon during a procedure, the arm assembly 100 further facilitates positioning of the primary heads-up display 108A such that the surgeon's head is level with the center of the primary heads-up display 108A. Even further, the arrangement and orientation of arm assembly 100, as well as the dimensions of primary heads-up display 108A, enable the surgeon's line of sight to any portion of the primary heads-up display 108A to be unobstructed.

During an ophthalmic surgical procedure, due to the position of the surgeon relative to the primary heads-up display 108A, views of the primary heads-up display 108A for one or more operating staff (other than the surgeon) may be obstructed or disposed at an angle such that the 3D visual effects provided by the display may be lost to such operating staff. Thus, to provide the staff with the same or similar quality view as seen by the surgeon, the arm assembly 100 may, in certain embodiments, include an optional secondary heads-up display 108B. In the example shown in FIGS. 1 and 2, the secondary heads-up display 108B is affixed to an articulating secondary horizontal support arm 112 coupled to the vertical column 104. Generally, the secondary heads-up display 108B may be utilized to show the same or different images as shown by primary heads-up display 108A, thereby facilitating a direct and unobstructed view of the surgical target site for operating staff and enhancing the ergonomics of the surgery for the entire surgical team.

In certain embodiments, to accommodate for different positions of the surgeon during different types of surgical procedures, the horizontal base arm 160, vertical column 104, and the horizontal support arm 102 are arranged and coupled such that the entire assembly 100 may be rotated by translation/rotation of the horizontal base arm 160 around the vertical axis A of the base column 162. In certain embodiments, the second end 166 of the horizontal base arm 160 may be rigidly coupled to the vertical column 104 and the vertical column 104 rigidly coupled to horizontal support arm 102 such that the horizontal support arm 102 extends parallel to the horizontal base arm 160. In such embodiments, when the optical head 110 is oriented with the optical axis E thereof perpendicular to, e.g., an operating room floor, the optical axis E may coincide and align with the vertical axis A of the vertical base column 162, thus forming a singular vertical axis. As a result, rotational translation of the horizontal base arm 160 about the vertical base column 162 will facilitate rotation of the optical head 110 with little to no X-Y translation of the optical head 110, which would otherwise require re-alignment of the optical head 110 after rotation of the assembly 100 to accommodate for the surgeon's position(s) during surgical procedures. Accordingly, axial alignment of the optical head 110 may be maintained with rotation of the assembly 100 between these different positions.

As shown in FIG. 1, with the rotation axis of the assembly 100 about the X-Y plane occurring at the vertical base column 162, any rotation of the optical head 110 will include the horizontal base arm 160 and the vertical column 104 simultaneously being rotated along with any heads-up displays 108 attached thereof. This allows for the entire assembly 100, including any heads-up displays 108 attached to the horizontal support arm 102 or the vertical column 104, to be rotated with a single translational movement of the assembly 100 about the vertical base column 162. This efficiently ensures that ergonomics are maintained for the surgeon when the assembly 100 is moved into the new position.

Figure 2:
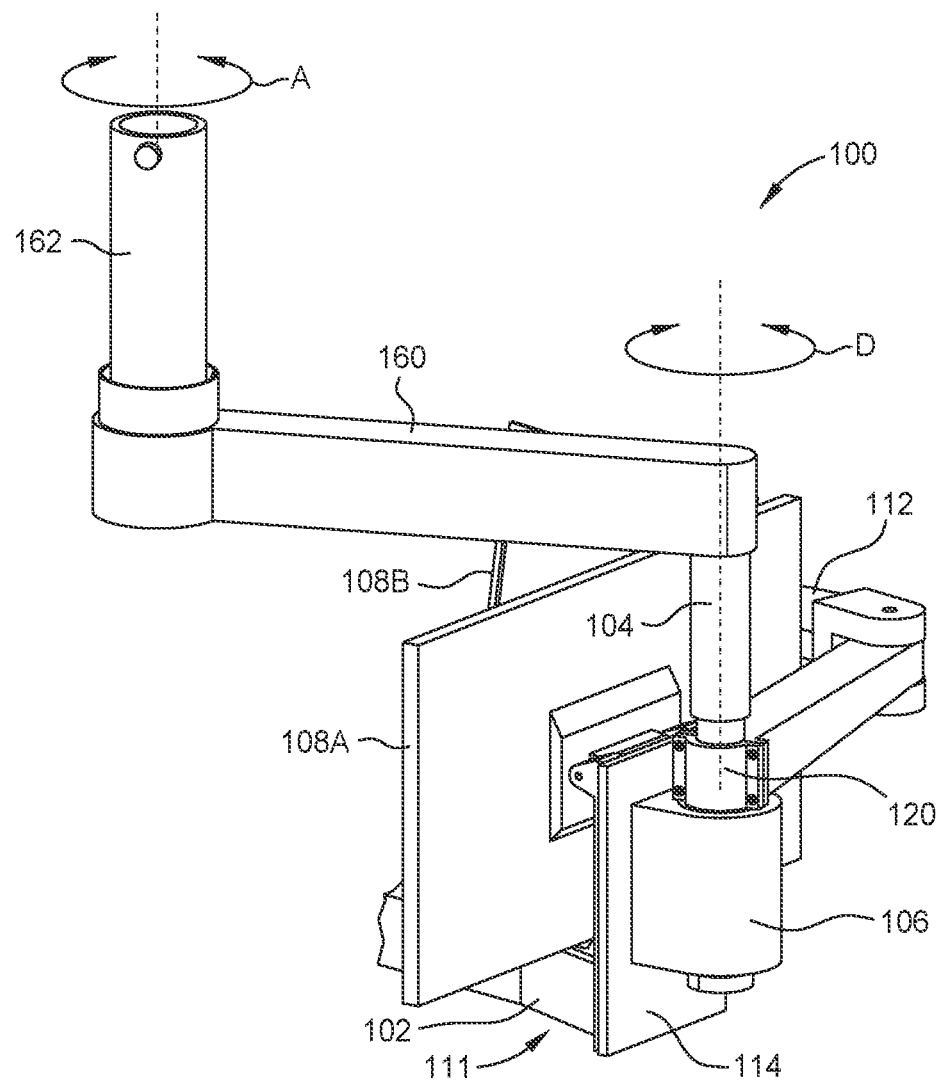
FIG. 2 illustrates another perspective view of the visualization system arm assembly of FIG. 1, in accordance with certain embodiments of the present disclosure.

FIG. 2 illustrates another perspective view of the arm assembly 100 of FIG. 1, in accordance with certain embodiments of the present disclosure. As shown, the horizontal support arm 102 of arm assembly 100 is coupled to the vertical column 104 at a first joint 106. In the example shown in FIG. 1, horizontal support arm 102 extends horizontally at about a 90-degree angle relative to a vertical axis D of vertical column 104. Generally, the horizontal support arm 102 may extend horizontally and/or diagonally (e.g., at a non-zero angle relative to a horizontal and a vertical plane) from the vertical column 104.

In certain embodiments, the horizontal support arm 102 may be configured to revolve or rotate about the vertical column 104 and the vertical axis D (e.g., by the vertical column 104 serving as an axle, pin, or cylinder). In such embodiments, the first joint 106 may comprise a revolute joint, which may include needle bearings or other similar bearings and/or devices to facilitate smooth rotational motion of the horizontal support arm 102 about the vertical column 104. In other embodiments, horizontal support arm 102 may be non-rotationally coupled to the vertical column 104. In further embodiments, the first joint 106 is configured to slide up and down along the vertical column 104 to allow the horizontal support arm 102 to translate vertically along the vertical axis D while maintaining the horizontal and/or diagonal orientation of the horizontal support arm 102. In such embodiments, first joint 106 comprises a sliding joint.

In certain embodiments, the horizontal support arm 102 has a length sized according to a monitor size (e.g., diagonal corner-to-corner length) of primary heads-up display 108A such that when the arm assembly 100 is used during a surgical procedure, the horizontal arm 102 facilitates an optimally ergonomic and immersive 3D experience/effect for the surgeon when viewing 3D images of the patient's eye. Such apportionment of the horizontal arm support 102 is referred to herein as the "ergonomic display distance."

In specific embodiments, the primary heads-up display 108A may comprise a 32-inch monitor display such that the ergonomic display distance for the surgeon is approximately 750 mm from the surgeon's eye. As such, the horizontal support arm 102 is sized such that when the arm assembly 100 is used by the surgeon to perform ophthalmic surgical procedures, the horizontal support arm 102 maintains the ergonomic 750 mm distance between the surgeon and the primary heads-up display 108A when the surgeon is positioned adjacent to the optical head 110, and opposite from and facing the primary heads-up display 108A.

In certain embodiments, the arm assembly 100 maintains the ergonomic display distance regardless of any movement or rotation of the optical head 110 necessitated by changes in the surgeon's position about the head of a patient. For example, in certain embodiments, due to both the optical head 110 and primary heads-up display 108A being affixed to the horizontal support arm 102, the primary heads-up display 108A is always correspondingly rotated and/or moved (e.g., translated) along with any movement or rotation of the optical head 110 by the surgeon. In certain other embodiments, however, the arm assembly 100 must be manually set to the ergonomic monitor distance by physically adjusting the position of primary display 108A.

As shown in FIG. 2, in certain embodiments, primary heads-up display 108A is affixed to horizontal support arm 102 by a first bracket 114 adjacent to a proximal end 111 of the horizontal support arm 102 near the first joint 106. The first bracket 114 may be configured to mount the primary heads-up display 108A in a fixed position on the horizontal support arm 102 with the backside of the display 108A adjacent to and against the vertical column 104, and the viewing side of the display 108A facing towards the optical head 110 and the distal end 109 of the horizontal support arm 102. In certain embodiments, the first bracket 114 may be configured with one or more additional hinges or joints to allow for primary heads-up display 108A to be tilted and moved to provide for dynamic adjustment for the primary heads-up display 108A.

Meanwhile, as described above, the secondary heads-up display 108B may be affixed to the vertical column 104 by an articulating secondary horizontal support arm 112 movably coupled to the vertical column 104. The articulating secondary horizontal support arm 112 may be configured to enable the secondary heads-up display 108B to be separately moved relative to the horizontal support arm 102 and/or primary heads-up display 108A.

Figure 3:
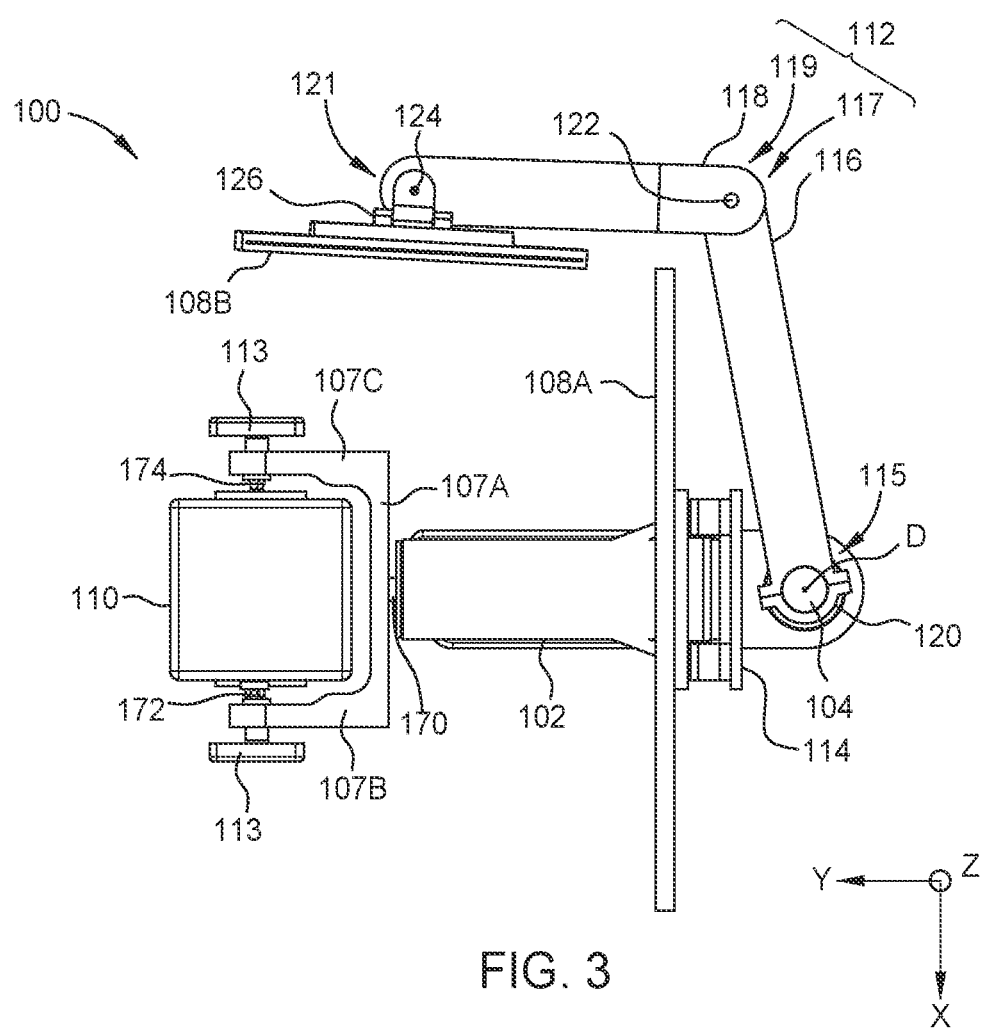
FIG. 3 illustrates a top-down view of an exemplary configuration of a portion of the visualization system arm assembly of FIG. 1 having a secondary horizontal support arm connected to a secondary heads-up display, in accordance with certain embodiments of the present disclosure.

FIG. 3 illustrates a top-down view of an exemplary configuration of a portion of the arm assembly 100 of FIG. 1, in accordance with certain embodiments of the present disclosure. The portion illustrated in FIG. 3 includes components disposed below section line A-A in FIG. 1. As shown, the articulating secondary horizontal support arm 112 includes two segments: a first, proximal segment 116, and a second, distal segment 118. A proximal end 115 of the proximal segment 116 is rotatably connected to vertical column 104 by a second revolute joint 120, which the proximal segment 116 extends horizontally or diagonally from. The second revolute joint 120 is configured to rotate proximal segment 116 about the vertical axis D extending through the vertical column 104, thereby providing horizontal movement for the proximal segment 116 along a horizontal X-Y plane parallel to the floor relative to vertical column 103. In the example shown in FIGS. 2 and 3, the second revolute joint 120 is positioned over (e.g., on top of) the first joint 106, though other arrangements are also contemplated. The second revolute joint 120 may also be configured to enable the proximal segment 116 to slide up and down along the vertical column 104 to adjust the vertical positioning of the secondary horizontal support arm 112 along the vertical X-Z plane relative to the vertical column 104.

A distal end 117 of proximal segment 116 is rotatably connected to the proximal end 119 of the distal segment 118 at a third revolute joint 122, which the distal segment 118 extends horizontally or diagonally from. The third revolute joint 122 is arranged such that an axis of rotation thereof is parallel to that of the second revolute joint 120, and therefore, perpendicular to the operating room floor and parallel to vertical axis D. Accordingly, the third revolute joint 122 facilitates X-Y motion of the distal segment 118 relative to the proximal segment 116.

A distal end 121 of the distal segment 118 further rotatably connects to optional secondary heads-up display 108B at a fourth revolute joint 124. The secondary heads-up display 108B may further comprise an adjustable mounting bracket 126 for affixing secondary heads-up display 108B to fourth revolute joint 124. The fourth revolute joint 124 is configured and oriented such that an axis of rotation thereof is parallel to that of vertical axis, and therefore, perpendicular to the operating room floor. Accordingly, the fourth revolute joint 124 facilitates horizontal rotation of the secondary heads-up display 108B along the X-Y plane about the distal end 121 of the distal segment 118.

As a whole, the proximal and distal segments 116, 118 of the articulating secondary horizontal support arm 112, as well as the revolute joints 120, 122, and 124, facilitate horizontal translation and movement of secondary heads-up display 108B parallel to the operating room floor. More particularly, the X-Y motion facilitated by the proximal and distal segments 116, 118 and the revolute joints 120, 122, and 124 enables a range of horizontal motion for secondary heads-up display 108B about the vertical column 104 from one side of the primary heads-up display 108A to the other, which enables the secondary heads-up display 108B to be viewed by the operating staff positioned around the surgeon during an ophthalmic surgical procedure. Additionally, because revolute joints 120, 122, and 124 are oriented parallel to one another, these rotational axes are not fighting against gravity, thereby providing greater payload for secondary horizontal support arm 112. In certain embodiments, the revolute joints 120, 122, and 124 may include needle bearings or similar devices to facilitate smooth rotational motion of the secondary heads-up display 108B about the vertical column 104.

Figure 4:
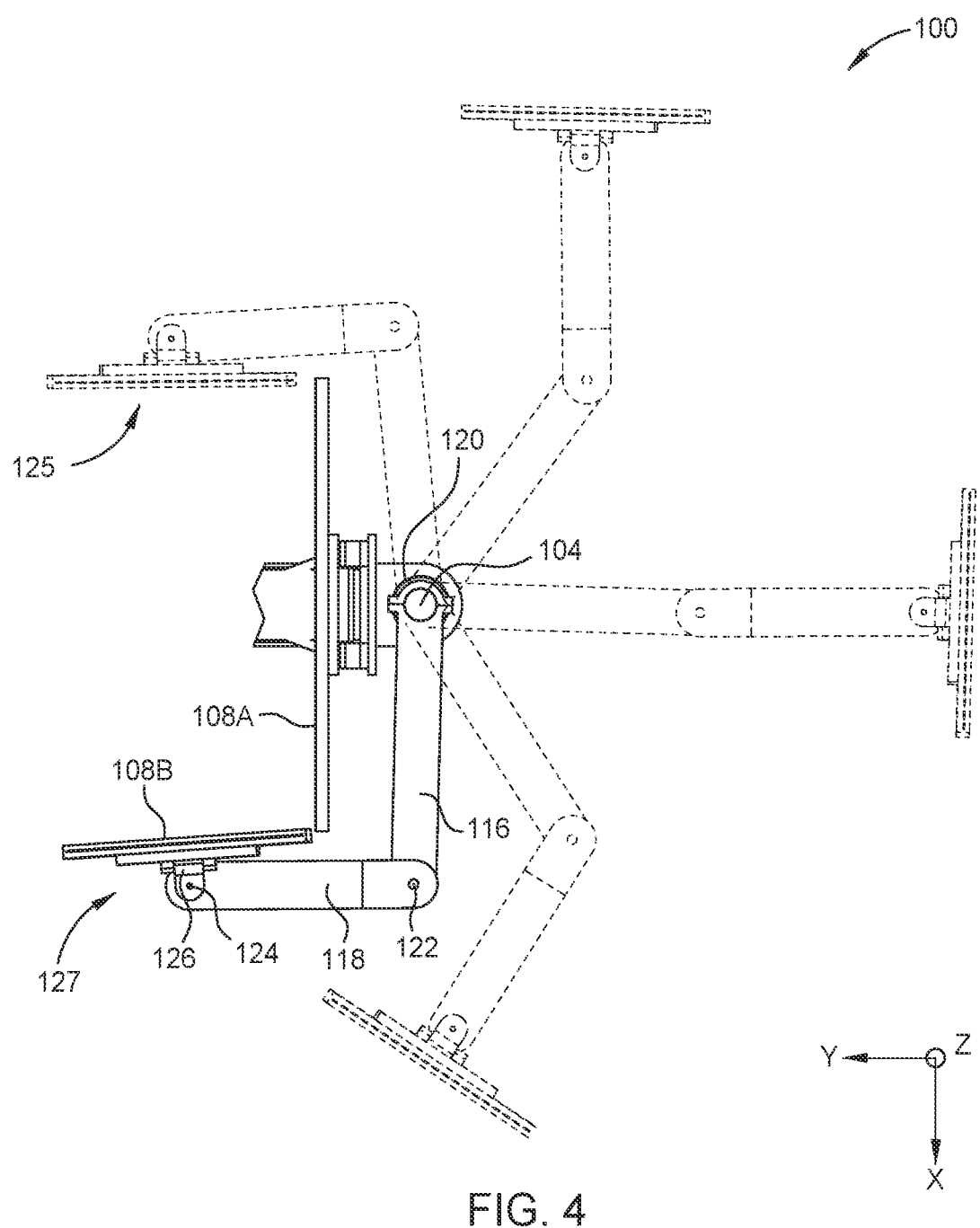
FIG. 4 illustrates a top-down view of the portion of the visualization system arm assembly of FIG. 3 with the secondary heads-up display being moved from a first position to a second position, in accordance with certain embodiments of the present disclosure.

FIG. 4 illustrates a top-down view of the secondary heads-up display 108B of FIG. 3 being moved, in accordance with certain embodiments of the present disclosure. As discussed above, the proximal and distal segments 116, 118 of the secondary horizontal support arm 112 provide secondary heads-up display 108B with horizontal translation and movement about vertical column 104. In the example shown in FIG. 4, secondary heads-up display 108B is moved from a first secondary heads-up display position 125, wherein the secondary heads-up display 108B is to the right of primary heads-up display 108A when viewed from the viewing side of primary heads-up display 108A, to a second secondary monitor display position 127, wherein the secondary heads-up display 108B is to the left of primary heads-up display 108A when viewed from the viewing side of primary heads-up display 108A. Such positions for the secondary heads-up display 108B may be utilized depending on the position of the surgeon in relation to the head of the patient during the surgery as well as the position(s) of the operating staff in the operating room. The secondary heads-up display 108B may be positioned to provide the operating staff a direct and unobstructed view of the surgical target site being operated on by the surgeon to further enhance the ergonomics of the surgery for the surgical team.

To change the secondary heads-up display 108B between positions 125 and 127, the proximal segment 116, distal segment 118, and secondary heads-up display 108 may each be individually rotated approximately 180 degrees about the second, third, and fourth revolute joints 122, 124, and 126, respectively, to swing secondary heads-up display 108B about the vertical column 104 between first position 125 and second position 127. In certain embodiments, the arm assembly 100 may be lockable in any given position between and including first position 125 and second position 127.

In certain aspects of the present disclosure, the arm assembly 100 may comprise more than one secondary heads-up display 108B connected to the vertical column 104, wherein each display is mounted to a corresponding horizontal support arm similar to the example shown in FIG. 4. In certain embodiments, more than one secondary heads-up display 108B may be connected to the same secondary horizontal support arm 112. In further embodiments, one or more secondary heads-up display 108B may also be connected to the horizontal support arm 102. Alternatively, the assembly 100 may not include any secondary heads-up displays 108B, and may be limited to the primary heads-up display 108A.

Returning now to FIG. 3, in certain embodiments, the horizontal support arm 102, first bracket 114, and vertical column 104 may also be movably coupled together such that the horizontal support arm 102 (and the optical head 110 connected thereto) may be moved relative to the vertical column 104 to provide X and Y motion to the optical head 110, without moving the rest of the arm assembly 100 (e.g. vertical column 104, horizontal base 160, and vertical base column 162). In certain embodiments, the horizontal support arm 102 may be movably coupled to the first bracket 114 along a plurality of sliding tracks (not shown) extending along the Y axis on the horizontal support arm 102 to enable movement of the horizontal support arm 102 relative to the first bracket 114 and the vertical column 104 along the Y axis. In certain embodiments, the first bracket 114 is movably coupled to the vertical column 104 along a plurality of slide tracks (not shown) extending along the X axis such that the first bracket 114 (as well as the horizontal support arm 102 and optical head 110 connected thereto) may be moved relative to the vertical column 104 along the X axis. Movement of the first bracket 114 along the X axis (with the position of the horizontal support arm 102 on the first bracket 114 fixed) thus enables the optical head 110 to be moved along the X axis relative to the vertical column 104 without moving the rest of the arm assembly 100 (e.g. vertical column 104, horizontal base 160, and vertical base column 162).

In certain embodiments, the movements of (1) the horizontal support arm 102 relative to the first bracket 114 in the Y direction and (2) the first bracket 114 relative to the vertical column 104 in the X direction, may be subject to motorized movement and control by the surgeon via one or more actuators, motors and/or controllers connected between the horizontal support arm 102, first bracket 114, and vertical column 104, and implemented with the assembly 100. When motorized, the assembly provides the surgeon with additional fine X and Y motion of the horizontal support arm 102/optical head 110 without further altering the setup of the assembly 100.

Figure 5A:
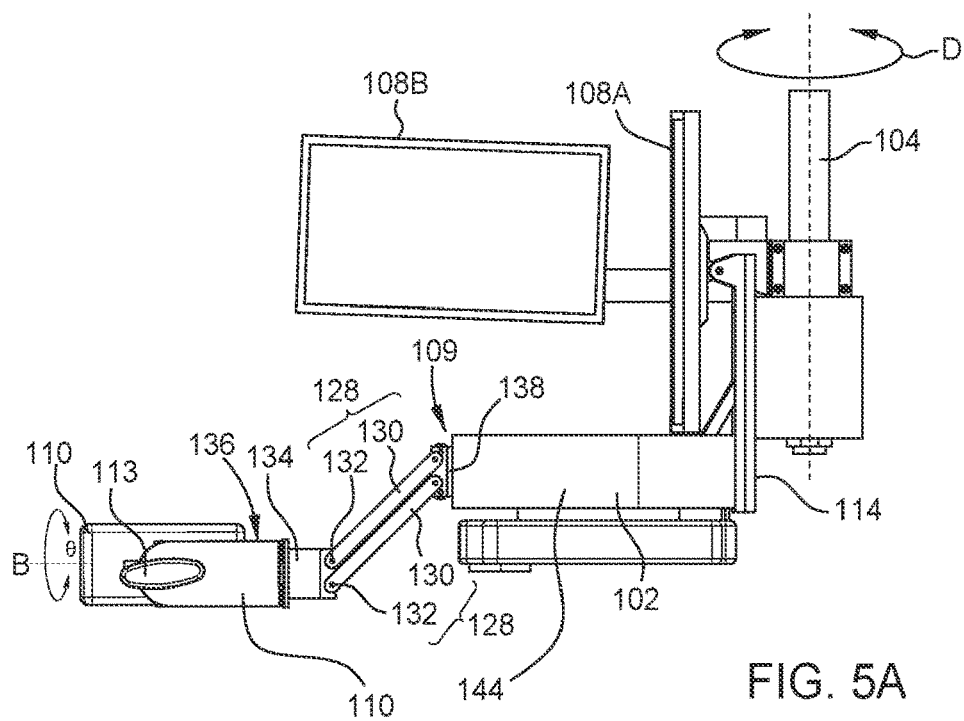
FIGS. 5A-5B illustrate a side and perspective view, respectively, of another exemplary configuration of a portion of the visualization system arm assembly of FIG. 1 with a horizontal support arm in an extended position, in accordance with certain embodiments of the present disclosure.
Figure 5B:
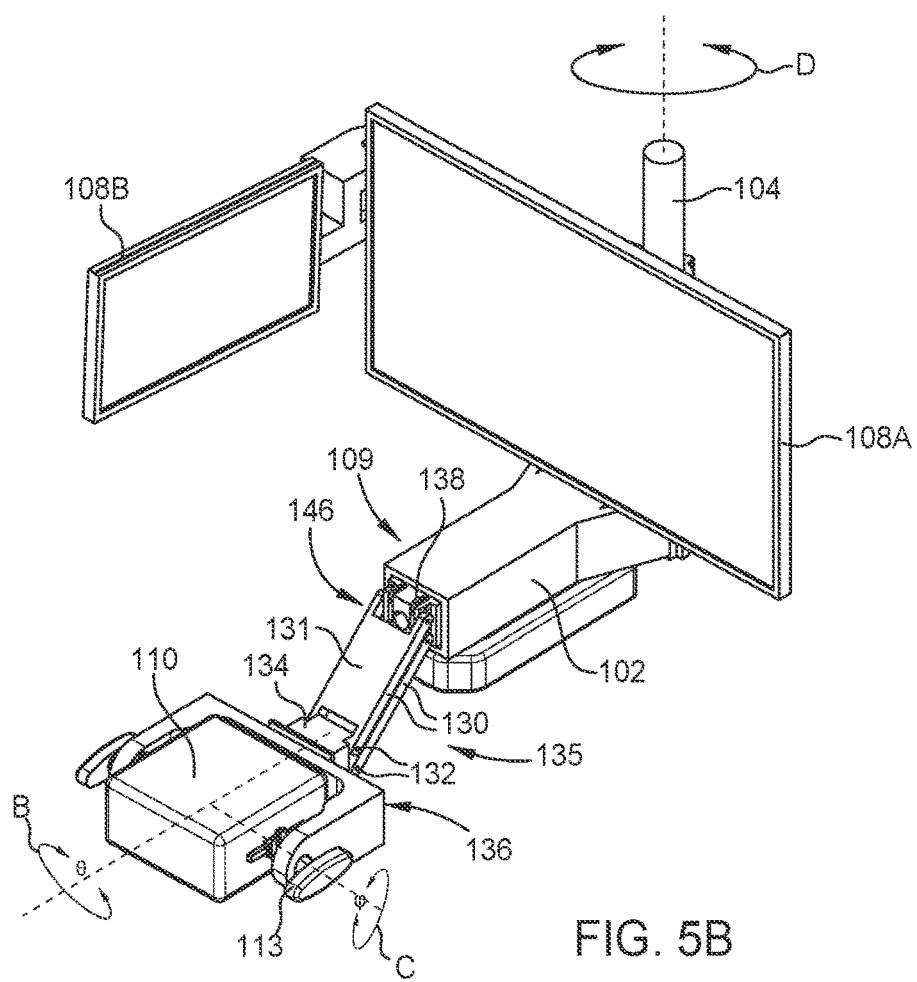
Figure 5C:
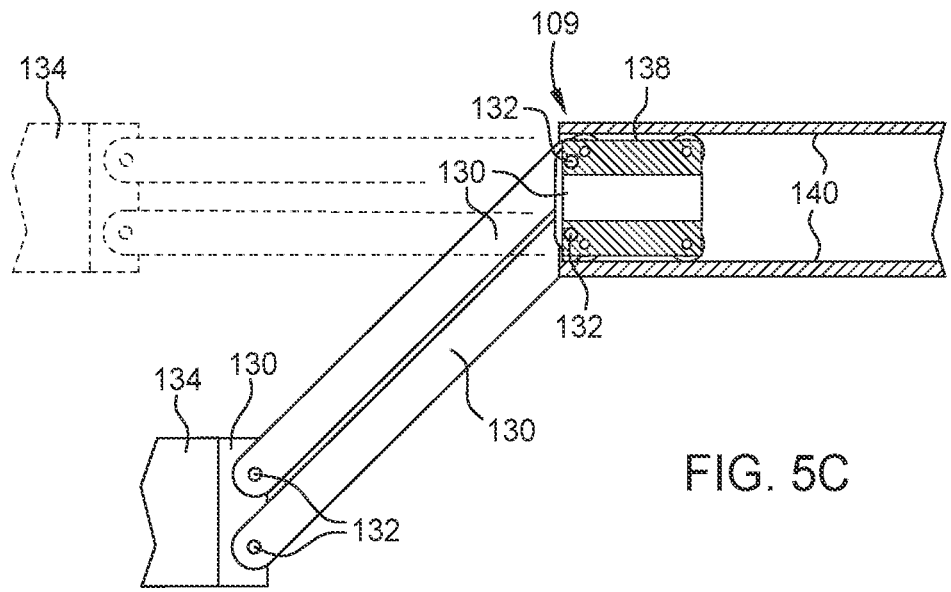
FIG. 5C illustrates a side view of a portion of the visualization system arm assembly of FIGS. 5A-5B, in accordance with certain embodiments of the present disclosure.

FIGS. 5A-5C illustrate side and perspective views, of another exemplary configuration of a portion of the arm assembly of FIG. 1 with an extension mechanism for the optical head 110, in accordance with certain embodiments of the present disclosure. Again, the portion illustrated in FIGS. 5A-5C include components disposed below section line A-A in FIG. 1. As shown, the horizontal support arm 102 may comprise an internal extension mechanism 135 configured to separate and extend the optical head 110 from the distal end 109 of the horizontal support arm 102 such that the optical head 110 may be vertically and longitudinally translated in relation to the horizontal support arm 102.

As discussed above, during ophthalmic surgical procedures, one of three primary positions surgeons may assume in relation to a patient's head is the patient superior position (shown in FIG. 7C, in relation to a patient 200) where the surgeon is positioned at the top of the patient's head. In such instances, the arm assembly 100 is positioned with the proximal end 111 of the horizontal support arm 102 disposed over the midsection of the patient and extending from the patient's chest to their head. Due to the positioning of the horizontal support arm 102, in some instances, the chest of a patient may contact the bottom of the horizontal support arm 102 before the optical head 110 is brought within working distance to the eye of the patient 200. To accommodate for the chest of the patient, the horizontal support 102 may be adjusted along the vertical column 104 to be raised over the patient's chest. The extension mechanism 135 of the optical head 110 may then be used to extend and lower the optical head 110 towards the head of the patient to properly align the optical head 110 over the target surgical site on the patient's head and position any imaging devices with the optical head 110 within a proper working distance thereof.

In FIG. 5C, a portion of horizontal support arm 102 (e.g., an outer shell thereof) is depicted in cross-section to illustrate the internal extension mechanism thereof, which facilitates a combination of longitudinal ("Y" movement) and vertical ("Z" movement) separation and translation of optical head 110 from the distal end 109 of the horizontal support arm 102. Specifically, the internal translation mechanism shown may enable the optical head 110 to be moved between a "home" and "extended" position in relation to the horizontal support 102, wherein in the "home" position, the optical head 110 is seated adjacent the distal end 109 of horizontal support arm 102 as shown in FIG. 1. In contrast, when the optical head 110 is in the "extended" position, the optical head 110 is separated from the distal end 109 of the horizontal support arm 102, as shown in FIGS. 5A-5C.

In certain embodiments, such as the examples shown in FIGS. 5A-5C, horizontal support arm 102 comprises a four bar parallelogram mechanism 128 affixed between a head base 134 rotatably connected to a proximal end 136 of the yoke 107, and a carriage 138 slidably connected to a plurality of rails 140 formed within a chamber 144 of the horizontal support arm 102. The four-bar parallelogram mechanism 128 enables passive, lockable vertical movement of optical head 110. The four-bar parallelogram mechanism 128 is formed by at least four bars 130 movably coupled by four horizontal revolute joints 132 that facilitate vertical motion of optical head 110 in relation to the carriage 138 within chamber 144 and the distal end 109 of the horizontal support arm 102. Revolute joints 132, in contrast to revolute joints 120, 122, and 124, are arranged such that each of the axes of rotation thereof are parallel to an operating room floor, i.e., parallel to the horizontal X-Y plane, and perpendicular with vertical axis D or vertical column 104. Such an arrangement enables vertical movement of optical head 110 perpendicular to the operating room floor plane, as shown in FIG. 5C, while maintaining the parallel orientation of revolute joints 120, 122, and 124. In certain embodiments, the four bar parallelogram mechanism 128 may be spring balanced and may comprise one or more springs disposed between revolute joints 132 thereof.

To effectuate longitudinal movement of the optical head 110, horizontal support arm 102 comprises the plurality of rails 140 and the carriage 138 within the chamber 144 of horizontal support arm 102. In certain embodiments, the plurality of rails 140 is formed along the interior surface of chamber 144 inside the horizontal support arm 102 and may extend between an opening 146 at the distal end of the horizontal support arm 102 towards the proximal end 111 of the horizontal support arm 102. The carriage 138 and the plurality of rails 140 may be slidably connected and configured as a dovetail slide mechanism such that the carriage 138 may slide inside the chamber 144 along the horizontal support 102 and plurality of rails 140 between the proximal end 111 and the opening 146. The movement of the carriage 138 along the longitudinal axis of the horizontal support arm 102 and parallel to the floor of the operating room therefore facilitates longitudinal movement of optical head 110 in relation to the horizontal support arm 102.

When the optical head 110 is in the "home position," the carriage 138 is positioned adjacent the proximal end 111 of the horizontal support arm 102 with the entire four-bar parallelogram mechanism 128 disposed inside the chamber 144 of the horizontal support arm 102. The head base 134 may then be fitted over the opening 146 such that the optical head 110 is connected to the horizontal support arm 102, and hence, in the "home" position. The sliding of the carriage 138 away from the proximal end 111 towards the opening 146, in turn, facilitates the extension of the horizontal support arm 102 and longitudinal movement of the optical head 110 away from the opening 146 to the "extended" position.

When the optical head 110 is in the "extended" position, the yoke 107 may still provide for both "pitch" and "roll" motion of the optical head 110. For example, when the optical head 110 is extended, the yoke 107 may still rotate about the head base 134, thus facilitating a "roll" motion of the optical head 110 about longitudinal axis B. When the optical head 110 is extended, the attachment points between the optical head 110 and the pair of yoke arms 107B, 107C facilitate a "pitch" motion of the optical head 110 about lateral axis C. In certain embodiments, in the extended position, the optical head 110 may be configured such that the control of the "pitch" and "roll" motion of the optical head 110 may be executed manually by the surgeon. Alternatively, the movement of the optical head 110 may be subject to motorized movement and control by the surgeon via one or more actuators, motors and/or controllers connected to the optical head 110 and implemented with the assembly 100. When motorized, the X, Y, and Z motion of the optical head 110 may allow for spherical motion around the focal point of the optics of the optical head 110. Accordingly, the support system described herein provides several benefits over conventional systems.

Figure 6A:
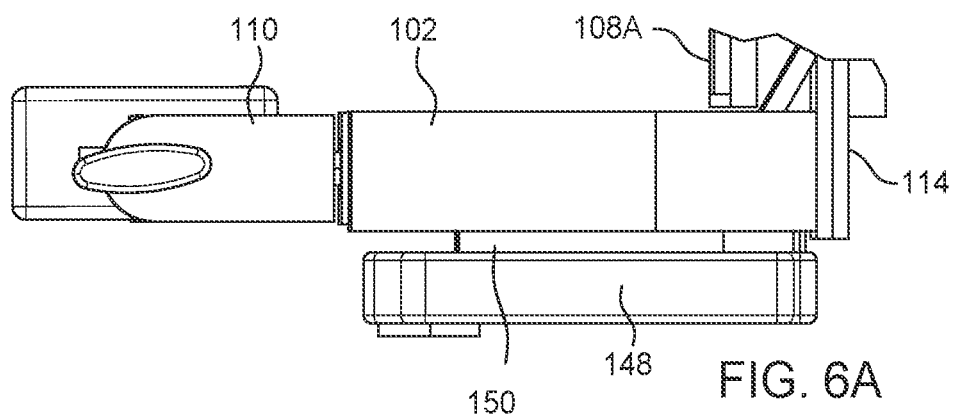
FIGS. 6A-6B illustrate side views of another exemplary visualization system arm assembly configured with a secondary optical device, in accordance with certain embodiments of the present disclosure.
Figure 6B:
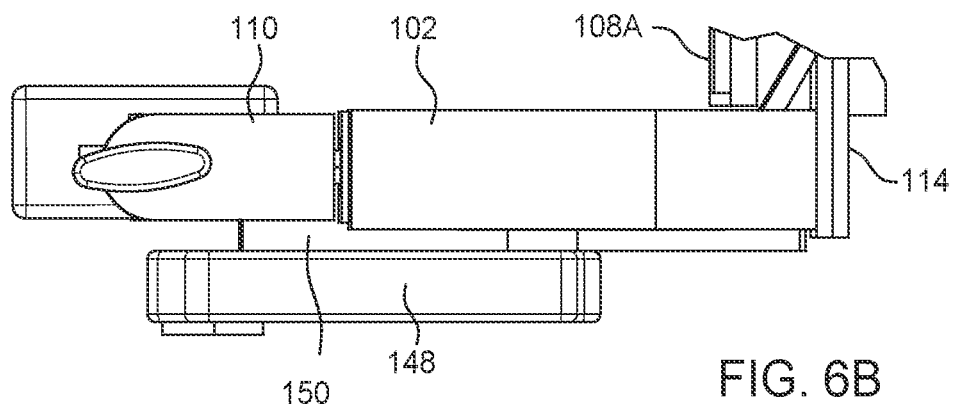

FIGS. 6A-6B illustrate side views of the arm assembly 100 configured with an additional optical device, in a "home" and "deployed" position, respectively, in accordance with certain embodiments of the present disclosure.

In the examples shown, in certain embodiments, the horizontal support arm 102 may comprise a secondary optical device 148 affixed along a bottom surface of the horizontal support arm 102. In certain embodiments, the secondary optical device 148 may comprise a diagnostic device such as an aberrometer, corneal topographer, autorefractor, and the like. The secondary optical device 148 may be slidably connected to the horizontal support arm 102 with, e.g., a dovetail slide 150 configured to enable the secondary optical device 148 to be moved along the bottom surface of the horizontal support arm 102. The dovetail slide 150 may facilitate the longitudinal movement or "Y" movement of the secondary optical device 148 along the X-Y plane parallel to the operating room floor. FIG. 6A shows the secondary optical device 148 in a "home" position beneath the horizontal support arm 102. To use the secondary optical device 148, the secondary optical device may be moved to a "deployed" position as shown in FIG. 6B, such that the secondary optical device 148 may be moved towards to optical head 110 to be aligned with the optical head 110 and positioned over a target surgical site. When the secondary optical device 148 is positioned over the target surgical site, the optical axis E of the optical head 110 and secondary optical device 148 may be coaxially aligned such that the secondary optical device 148 is positioned over the same target site previously viewed by the optical head 110.

Figure 7B:
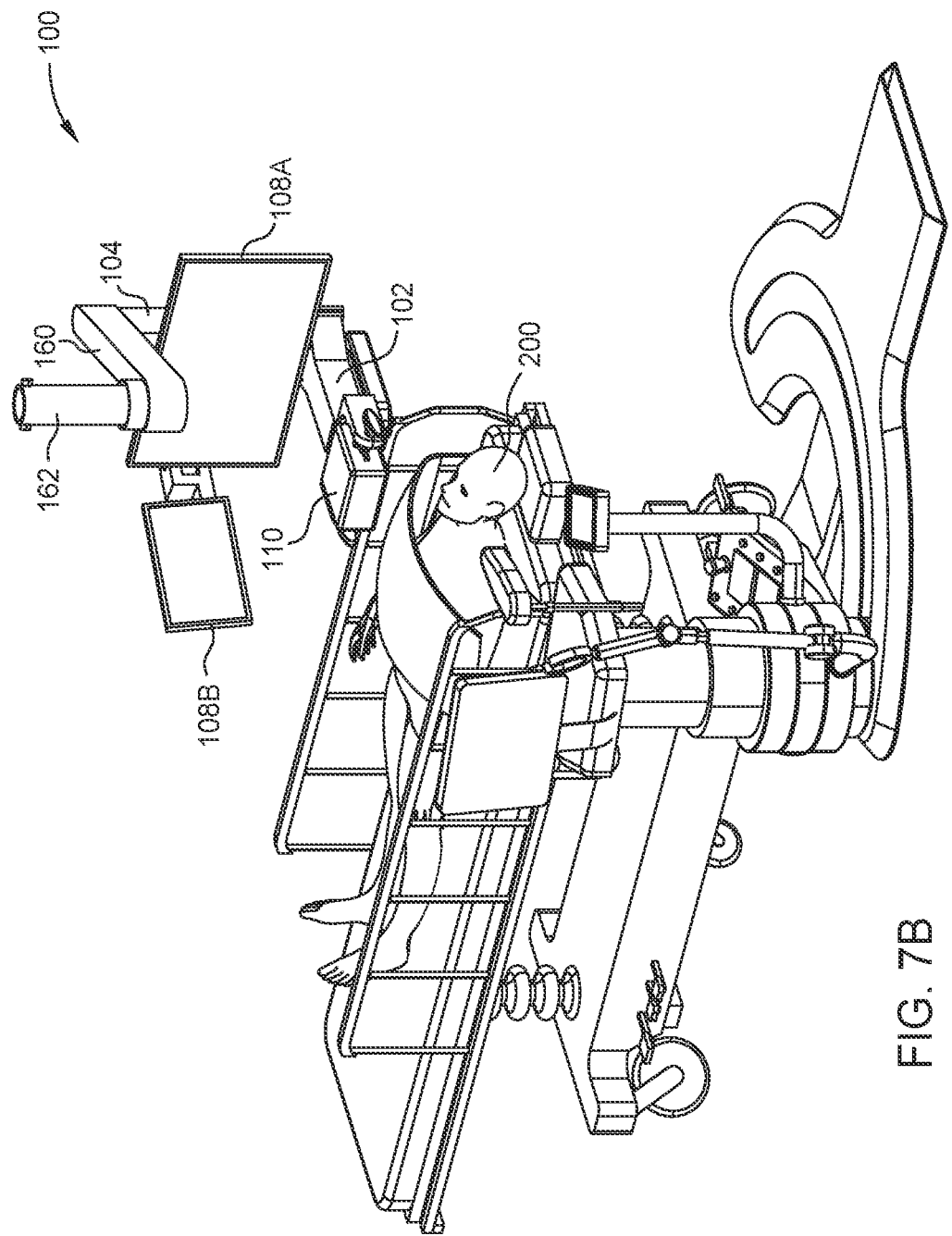
Figure 7C:
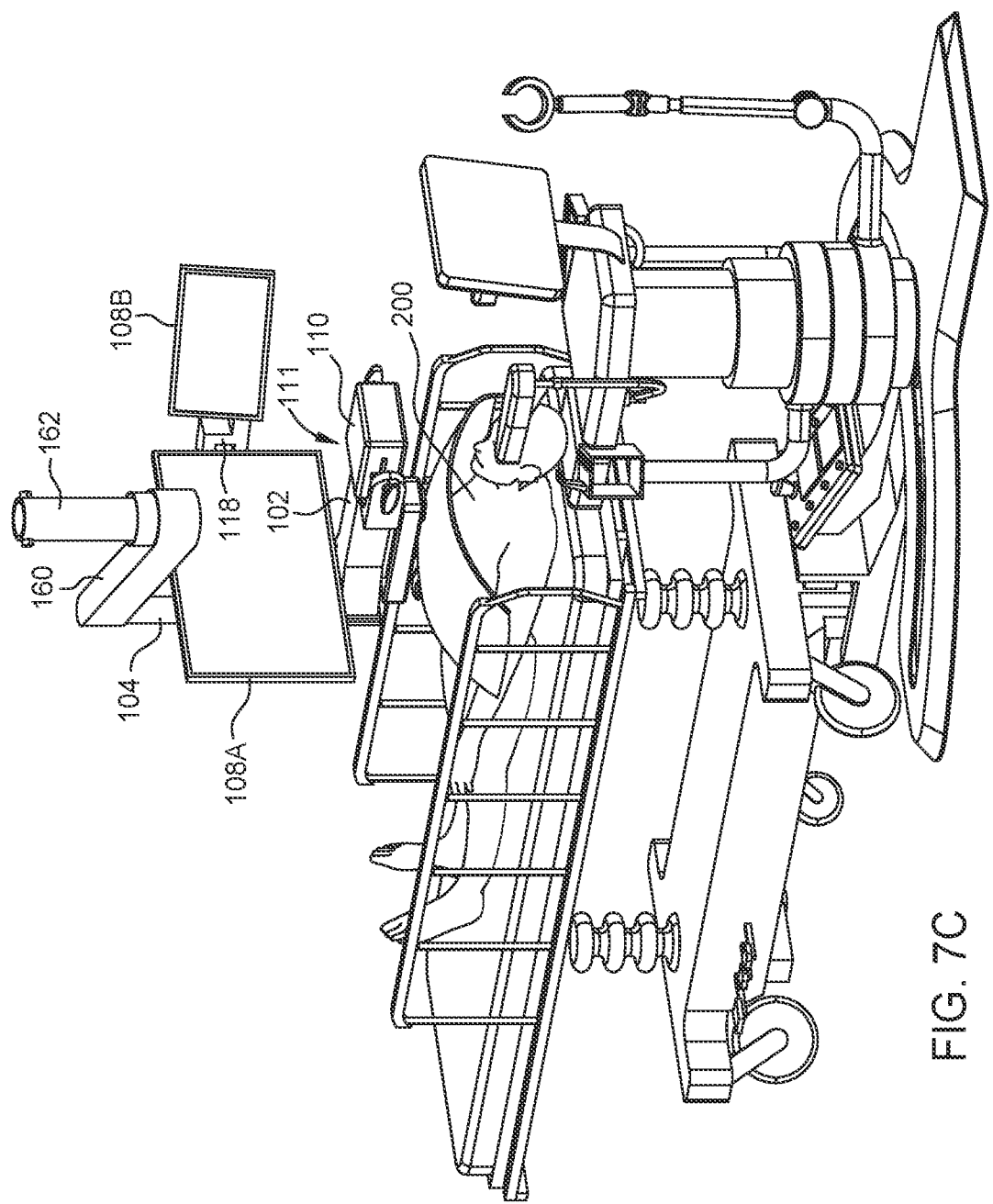

FIGS. 7A-7C illustrate the arm assembly of FIG. 1 positioned in a left temporal, right temporal, and superior position about a patient 200, respectively, in accordance with certain embodiments of the present disclosure.

As discussed above, during ophthalmic surgical procedures, there are three primary positions that the surgeon assumes for various procedures in relation to the patient's head—left temporal, right temporal and superior. FIG. 7A shows the assembly 100 oriented for a left temporal position in which the surgeon stands facing the left side of the patient's head. FIG. 7B shows the assembly 100 oriented for a right temporal position wherein the surgeon stands facing the right side of the patient's head. And lastly, FIG. 7C shows the assembly 100 oriented for a superior position wherein the surgeon stands facing the top of the patient's head.

To adjust the assembly 100 between each of the above three positions, the horizontal base arm 160 may be rotated about the base revolute joint 168, thereby rotating the orientation of the optical head 110 and primary heads-up display 108b about the horizontal X-Y plane parallel to the operating room floor. For example, to change the assembly 100 from the right temporal position shown in FIG. 7B to the superior position shown in FIG. 7C, the base arm 160 may be rotated counter-clockwise 90 degrees about the vertical base column 162. When the base arm 160 is rotated, the optical head 110, the support arm 102, the vertical column 104, and the primary heads-up display 108A are also rotated therewith. The simultaneous corresponding rotation of the primary heads-up display 108a and the horizontal support arm 102, which maintains the ideal ergonomic distance between the surgeon and the primary display 108A, facilitates maintenance of the ideal ergonomics for the surgeon when the system is adjusted between positions, without the need for further adjustments of the primary display 108A by the surgeon or the surgery team. As such, the assembly 100 discussed herein is extremely efficient in maintaining ergonomics when movements of the optical head 110 and corresponding surgical visual systems need to be made to accommodate for a different surgical position by the surgeon.

In summary, embodiments of the present disclosure include imaging and display support arms for ophthalmic visualization systems with improved ergonomics for both a surgeon and their operating staff. For example, the arrangement of both the primary heads-up display and the optical head on the horizontal support arm provides the surgeon with unobstructed direct line of sight at all times to the primary heads-up display thereby providing the surgeon with the most favorable ergonomics possible during the surgery. Additionally, the utilization of a movable secondary horizontal support arm facilitates a direct and unobstructed view of the surgical target site on a secondary heads-up display for the other operating staff, thereby further enhancing the ergonomics of the surgery for the entire surgical team. Still further, the combined four-bar parallelogram and dovetail slide mechanism driven extension of the optical head facilitates utilization of the digital surgical visualization systems while avoiding interference(s) or impediments as caused by the horizontal support arm contacting the patient's chest, and further enables visualization display screens to be positioned and maintained directly in front of the surgeon. Accordingly, the support system described herein provides several benefits over conventional systems.

Although cataract and vitreoretinal surgeries are discussed as an example of surgical procedures that may benefit from the described embodiments, the advantages of the surgical devices and systems described herein may benefit other surgical procedures as well.

While the foregoing is directed to embodiments of the present disclosure, other and further embodiments of the disclosure may be devised without departing from the basic scope thereof, and the scope thereof is determined by the claims that follow.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. A support system for an ophthalmic visualization system, the support system comprising:
 a base column;
 a first arm connected to the base column, wherein the first arm is configured to rotationally translate along a first horizontal plane and about a first revolute joint at the base column;
 an optical head coupled to a distal end of the first arm; and
 a first display coupled to a top surface of the first arm.

2. The support system of claim 1, further comprising:
 a base arm comprising a proximal end and a distal end, wherein the first arm being connected to the base column comprises the proximal end of the base arm coupled to the base column via the first revolute joint, the distal end of the base arm connected to a support column extending between the base arm and a proximal end of the first arm, and wherein rotational translation of the base arm along a second horizontal plane and about the first revolute joint simultaneously causes rotational translation of the first arm along the first horizontal plane.

3. The support system of claim 2, wherein rotational translation of the base arm about the base column simultaneously rotationally translates the optical head, the first arm, the support column, and the first display coupled to the first arm about the base column.

4. The support system of claim 2, wherein rotational translation of the base arm about the base column rotates the optical head about a longitudinal base axis in alignment with an optical axis of the optical head.

5. The support system of claim 2, further comprising an articulating second arm connected to the support column, the articulating second arm comprising:
 a first segment comprising a proximal end and a distal end, the first segment configured to rotationally translate along a third horizontal plane and about a second revolute joint at the proximal end of the articulating second arm, the first segment coupled to the support column via the second revolute joint;
 a second segment comprising a proximal end and a distal end, the second segment configured to rotationally translate along the third horizontal plane and about a third revolute joint at the proximal end thereof, the second segment coupled to the first segment via the third revolute joint; and
 a second display coupled to the distal end of the second segment and configured to rotationally translate along the third horizontal plane via a fourth revolute joint, the second display coupled to the second segment via the fourth revolute joint.

6. The support system of claim 4, wherein the first, second, third, and fourth revolute joints are arranged parallel with one another.

7. The support system of claim 1, wherein the optical head comprises one or more of the following devices: a microscope, a digital microscope, a compound microscope, a digital compound microscope, a digitally assisted microscope, a digital microscope camera, a digital camera, and an ophthalmic 3D stereo microscope camera.

8. The support system of claim 1, further comprising:
 a yoke connecting a proximal end of the optical head to a distal end of the first arm, wherein the yoke is configured to rotationally translate about a longitudinal axis extending through the first arm via a second revolute joint at the distal end of the first arm, and wherein the optical head is configured to rotationally translate about a lateral axis extending perpendicular to the longitudinal axis via one or more yoke revolute joints connecting the optical head to the yoke.

9. The support system of claim 8, wherein the rotational translation of the yoke about the longitudinal axis provides "roll" motion to the optical head relative to the first arm.

10. The support system of claim 8, wherein the rotational translation of the optical head at the one or more yoke revolute joints on the yoke about the lateral axis provides "pitch" motion to the optical head relative to the yoke.

11. The support system of claim 1, wherein the first arm further comprises a dovetail slide mechanism extending between the optical head and the first arm to facilitate extension of the optical head away from the first arm along a longitudinal axis of the first arm.

12. The support system of claim 11, wherein the first arm further comprises a four-bar parallelogram mechanism extending between the optical head and the dovetail slide mechanism to facilitate vertical translation of the optical head from the first arm.

13. The support system of claim 11, further comprising an opening at the distal end of the first arm and a chamber extending from the opening towards the proximal end of the first arm, wherein the dovetail slide mechanism comprises a carriage slidably connected to the first arm inside the chamber.

14. The support system of claim 12, wherein the dovetail slide mechanism and four-bar parallelogram mechanism facilitate separation and extension of the optical head from the first arm.

15. The support system of claim 2, wherein the first revolute joint is configured to slide along the support column to facilitate vertical movement of the first arm thereof.

16. The support system of claim 5 wherein the second revolute joint is configured to slide along the support column to facilitate vertical movement of the articulating second arm thereof.

17. The support system of claim 12, wherein the four-bar parallelogram mechanism further compromises one or more springs to facilitate configuring the four-bar parallelogram mechanism to be spring balanced.

18. The support system of claim 1, furthering comprising a secondary optical device coupled along a bottom surface of the first arm.

19. The support system of claim 5, wherein the articulating second arm facilitates translation of the second display along the third horizontal plane to move between a first position on a first side of the first display and a second position on a second side of the first display.

20. The support system of claim 1, wherein the first arm maintains an ideal ergonomic distance between a vertical plane at a distal end of the optical head and the first display when the first arm is adjusted relative to the base column.

* * * * *